US007041854B2

(12) United States Patent
Quesnel et al.

(10) Patent No.: US 7,041,854 B2
(45) Date of Patent: May 9, 2006

(54) PROCESS FOR THE PREPARATION OF AN XANTHOPHYLL

(75) Inventors: Yannick Quesnel, Lasne (BE); Richard Flacher, Lyons (FR)

(73) Assignee: Adisseo France S.A.S., Antony (FR)

( * ) Notice: Subject to any disclaimer, the term of this patent is extended or adjusted under 35 U.S.C. 154(b) by 318 days.

(21) Appl. No.: 10/474,899

(22) PCT Filed: Apr. 18, 2002

(86) PCT No.: PCT/EP02/05455

§ 371 (c)(1),
(2), (4) Date: Dec. 2, 2003

(87) PCT Pub. No.: WO02/085831

PCT Pub. Date: Oct. 31, 2002

(65) Prior Publication Data

US 2004/0074843 A1    Apr. 22, 2004

(30) Foreign Application Priority Data

Apr. 24, 2001 (EP) .................................. 01109976

(51) Int. Cl.
C07C 45/27 (2006.01)
(52) U.S. Cl. ...................... 568/342; 568/347; 568/377

(58) Field of Classification Search ................. 568/342, 568/347, 377
See application file for complete search history.

(56) References Cited

U.S. PATENT DOCUMENTS

| 4,105,855 | A | * | 8/1978 | Schulz et al. ................ 560/190 |
| 4,212,827 | A | | 7/1980 | Paust et al. .................. 568/347 |
| 4,585,885 | A | | 4/1986 | Bernhard et al. ........... 556/436 |

OTHER PUBLICATIONS

Ma et al. Enhanced production of free trans-astaxanthin by oxidative stess in the cultures of the green microalga *Chlorococcum* sp. Process Biochemistry, 2001, vol. 36, p 1175-1179.*
J. Paust; "Recent progress in commercial retinoids and carotenoids"; Pure & Appl. Chem., vol. 63, No. 1; 1991; pp 45-58.

* cited by examiner

*Primary Examiner*—Sikarl A. Witherspoon
(74) *Attorney, Agent, or Firm*—Oliff & Berridge, PLC

(57) ABSTRACT

The present invention relates to a process for the preparation of an xanthophyll, and in particular to a process for the preparation of an xanthophyll through the oxidation of a carotenoid in the presence of hydrogen peroxide and an iodine-containing compound. In particular, the process of the invention applies to the oxidation of beta-carotene to produce canthaxanthin, and to the oxidation of lutein or zeaxanthin to produce astaxanthin.

12 Claims, 2 Drawing Sheets

PROCESS FOR THE PREPARATION OF AN XANTHOPHYLL

The present invention relates to a process for the preparation of an xanthophyll, and in particular to a process for the preparation of an xanthophyll through the oxidation of a carotenoid in the presence of hydrogen peroxide and an iodine-containing compound Xanthophylls are a particular group of carotenoids. Carotenoids include hydrocarbons such as carotenes and oxygenated alcoholic derivatives thereof such as xanthophylls. Representative examples of carotenes include alpha-carotene, beta-carotene and lycopene. Representative examples of xanthophylls include lutein, zeaxanthin, capsorubin, capsantlnn, astaxanthin, and canthaxanthin. Carotenoids are important food dying agents and animal feed additives.

Methods of production of canthaxanthin are known through the oxidation of betasarotene with sodium chlorate, sodium bromate, sodium iodate, sodium perchlorate, sodium meta-perchlorate, in the presence of a catalyst such as iodine, bromine, selenium dioxide, vanadium pentoxide, or osmium tetraoxide as disclosed in U.S. Pat. No. 4,212,827 and European Patent Application EP 1 059 290.

The production of astaxantin from lutein or zeaxanthin is known from WO 99/26914 This process does not include an oxidation step.

In the aforementioned processes, the oxidation reagents, alkaline perchlorates, chlorates, bromates or iodates are introduced in excess in relation to the stoichiometric amount needed. In general four equivalents are theoretically needed. Moreover, these reagents are quite hazardous and expensive, and these processes produce non-negligible quantities of salts so that effluent treatments have to be taken into account It has been found in the present invention that xanthophylls can be produced in a short time and in an industrially advantageous manner which avoids the aforementioned problems.

Accordingly, the present invention provides a process for producing a mono- or poly-oxidised xanthophyll which process comprises oxidising a carotenoid of a lower oxidation state than the xanthophyll to be produced with an aqueous solution of hydrogen peroxide and an organic solvent, said solvent being immiscible with water, wherein said oxidation reaction is carried out in the presence of an iodine-containing compound.

For the purposes of the present invention, a mono- or poly-oxidised xanthophyll refers to an xanthophyll comprising at least one oxygen. Examples of such xanthophylls are lutein, zeaxanthin, capsorubin, capsanthin, canthaxantin and astaxanthine. The carotenoid of a lower oxidation state is a carotenoid such as beta-carotene, lutein or zeaxanthin.

In a preferred embodiment, the process of the invention is a process for producing canthaxanthin and the carotenoid of a lower oxidation state is beta-carotene.

In another preferred embodiment, the process of the invention is a process for producing astaxanthin and the carotenoid of a lower oxidation state is either lutein or zeaxanthin.

The process of the present invention involves the use of an aqueous solution of hydrogen peroxide. Suitably, the concentration of said solution is from 1 to 85% by weight. Most preferably, the concentration is from 25 to 55% by weight.

The process of the invention requires an organic solvent that is immiscible with water. Examples of such organic solvents include halogenated hydrocarbons, such as methylene chloride, chloroform, carbon tetrachloride, monochlorobenzene, or dichloroethane; aromatic hydrocarbons such as benzene, toluene, or xylene; aliphatic hydrocarbons such as pentane, hexane, cyclohexane, or heptane; ethers such as diethyl ether, di iodopropyl ether, or methyl t-butyl ether, an esters such as methyl acetate, ethyl acetate, butyl acetate, or isopropyl acetate. The organic solvent can be used in one or more forms. The preferred solvent is a halogenated hydrocarbon, especially monochlorobenzene and chloroform. The amount of organic solvent may be from 2 to 300 times the weight of the carotnenoid.

The process of the invention may be carried out in the presence of water, that is to say water in addition to the aqueous solution of hydrogen peroxide. The water may be present in an amount of 0.2 and 50 times the weight of the carotenoid, preferably from 10 to 30 times the weight of the carotenoid.

The process of the present invention requires an iodine-containing compound. This compound initiates the oxidation reaction. Iodine-containing compounds that can be used in the process of the present invention are iodine, iodine halides, or metal iodide or a mixture thereof. Two or more of these compounds may be present in the reaction mixture. Examples of iodine halide that can be used in the present invention include iodine chloride, iodine trichloride, iodine tribromide, and iodine tribromide. Examples of metal iodide that can be used in the present invention include lithium, sodium, potassium, silver, calcium, magnesium, copper(I) and copper(II) iodides. The preferred compound is iodine or an alkali metal iodide such as potassium or sodium iodide.

The total amount of iodine-containing compound is suitably from 1 to 40% by mole of the amount of carotenoid, preferably from 15 to 25% by mole.

Where two or more iodine-containing compounds are added to the reaction mixture comprising the carotenoid, the aqueous solution of hydrogen peroxide and the organic solvent, these compounds may be added separately or in the form of a mixture thereof. The iodine-containing compound may be added to the reaction mixture either continuously, portion by portion, or all at once. Preferably, said iodine-containing compound is added as a single aliquot.

The iodine-containing compound may be added to the reaction mixture either in the solid form or in the form of a solution in an appropriate solvent, i.e. where it is a metal iodide, the suitable form is an aqueous solution and where it is iodine or iodine halide, the suitable form is in an organic solvent.

When beta-carotene is used as a substrate to be oxidised by the process of the invention, the process leads to the production of canthaxanthin. Beta-carotene is a commercially available compound, which can also be produced by any known method, such as for example the method described in European Patent Application No. 00128048.6.

When lutein or zeaxanthin is used as substrates to be oxidised by the process of the invention, the process leads to the production of astaxanthin. Lutein and zeaxanthin are commercially available compounds, which can also be obtained by extaction from natural material, especially from marigold flowers (*Tagetes erecta*), or produced by any known method.

The process of the present invention may be carried out at a pH of from 2 to 10, preferably, from 5 to 8 and under a temperature of from −10° C. to 50° C., preferably from 20° C. and 30° C.

The process of the invention is preferably carried out in the atmosphere of an inert gas such as nitrogen or argon.

The oxidation reaction according to the present invention is preferably conducted under appropriate stirring.

The progress of oxidation according to the present invention can be detected by any suitable analytical means know to the man skilled in the art. In particular, one can use thin layer chromatography (TLC) or high-performance liquid chromatography (HPLC). The time until the reaction reaches completion differs depending on the reaction conditions, but is in general from 5 to 300 minutes.

After the reaction has reached completion, the produced xanthophyll can be isolated by usual methods known to the man skilled in the art. In particular, the method may comprise leaving the reaction mixture to stand still to permit the separation of the two phases, i.e. a water phase and an organic phase; collecting the organic phase; washing said organic phase if necessary with an aqueous reducing solution (for example, alkali metal thio sulphate or alkali metal sulphate), and removing the organic solvent from the organic phase to collect the crystalline crude xanthophyll.

The crude xanthophyll may then be isomerised into its trans-isomer. Isomerisation can be achieved by classical methods such as thermal isomerisation in hot solvent (water, an alcohol such as methanol, ethanol or isopropanol; a ketone such as acetone, methyl ethyl ketone; or a hydrocarbon such as hexane, cyclohexane or heptane).

The produced xanthophyll can also be further purified by classical methods known by the skilled man such as column chromatography or crystallisation.

The present invention will now be ill by way of the following examples:

EXAMPLE 1

Production of Canthaxanthin from β-Carotene with Chloroform as Solvent

Figure 1:
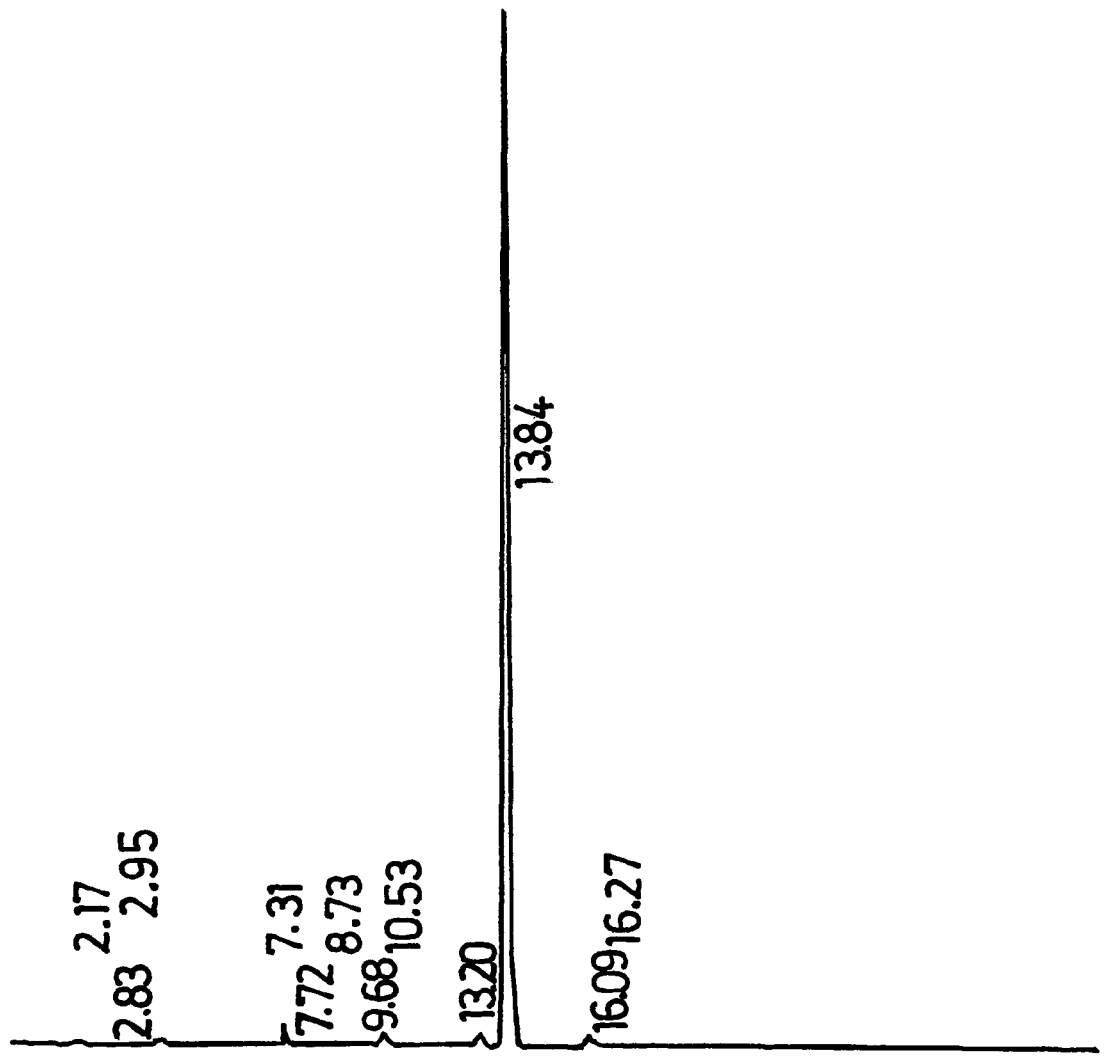
FIG. 1 shows an HPLC analysis of the reaction product canthaxanthin.

A three neck flask, equipped with a dropping funnel, a thermometer and a reflux condenser, was charged β-Carotene (1.988 g, 3.59 mmol, 97%), chloroform (70 ml, 103.7 g), hydrogen peroxide (30% wt 4.09 eq; 14.69 mmol, 1.5 ml, 1.665 g). The reaction mixture was then sired at ambient temperature and iodine solution (0.25 eq, 0.90 mmol, 0.228 g in 6 ml of chloroform) was then added in one portion. The resulting mixture was stared for 5 hours. At this time, the β-Carotene disappeared and the pH of the solution was 7. 20 ml of thio sulphate solution was then added and the resulting mixture stirred for 15 minutes. The mixture was then allowed to stand still to allow separation into the 2 phases (upper phase=water; lower phase=organic phase). The organic phase was collected and the solvent removed under reduced pressure affording the crude crystalline product. This crude product was mixed with 7.5 ml of acetone and heated under refluxed over night. After cooling to 4° C., the cristalline canthaxanthine was collected by filtration (837 mg, Yield 40%, all trans>98%) Analysis by HPLC verified that the product was canthaxanthine (FIG. 1). The mother liquor contained canthaxanthine as a mixture of isomers (trans/cis ratio 50/50).

EXAMPLE 2

Production of Canthaxanthin from β-Carotene with Monochlorobenzene as Solvent

Figure 2:
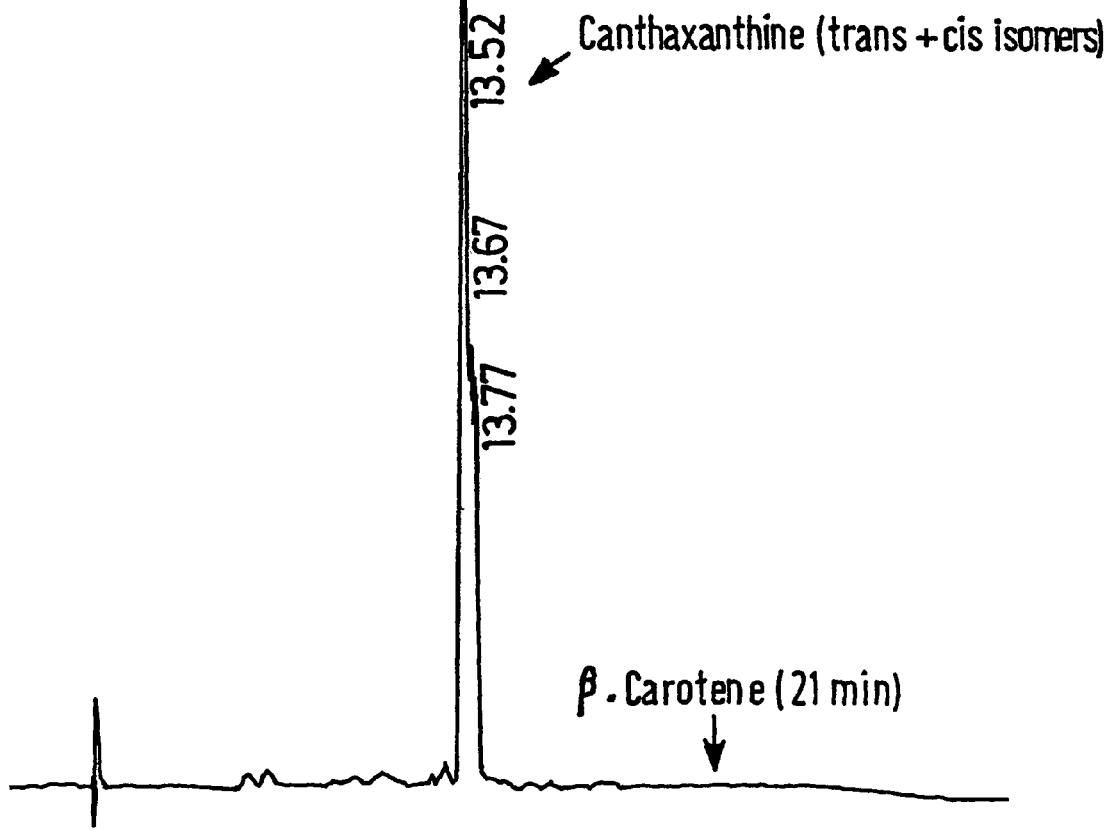
FIG. 2 shows an HPLC analysis of the reaction product canthaxanthin as a mixture of isomers.

A three neck flask, equipped with a dropping funnel, a thermometer and a reflux condenser, was charged β-Carotene (1 g, 1.863 mmol, 97%), monochlorobenzene (20 ml, 22.14 g), hydrogen peroxide (30% wt; 4.2 eq; 7.823 mmol, 0.90 ml, 0.99 g). The reaction mixture was then stirred at ambient temperature and solid iodine (0.25 eq, 0.4655 mmol, 118 mg) was then added in one portion. The resulting mixture was stirred for 90 minutes. At this time, β-Carotene disappeared and the pH of the solution was 7. The resulting reaction mixture was allowed to stand still to separate into the 2 phases (upper phase=water; lower phase=organic phase). The organic phase was collected and washed successively with 15 ml of 2% aqueous sodium thio sulphate solution and 15 ml of water. The solvent was removed under reduced pressure affording 1.1 g of the crude crystalline product that was identified as canthaxanthin (mixture of isomers) by HPLC (FIG. 2).

What is claimed is:

1. A process for producing a mono- or poly-oxidised xanthophyll which process comprises oxidising a carotenoid of a lower oxidation state than the xanthophyll to be produced with an aqueous solution of hydrogen peroxide and an organic solvent, said solvent being immiscible with water, wherein said oxidation reaction is carried out in the presence of an iodine-containing compound.

2. A process according to claim 1, wherein said mono- or poly-oxidised xanthophyll is cantaxanthin and said carotenoid of a lower oxidation state is beta-carotene.

3. A process according to claim 1, wherein said mono- or poly-oxidised xanthophyll is astaxanthin and said carotenoid of a lower oxidation state is lutein or zeaxanthin.

4. A process according to claim 1, wherein said aqueous solution of hydrogen peroxide is at a concentration comprised from 1 to 85% by weight.

5. A process according to claim 4, wherein said wherein said aqueous solution of hydrogen peroxide is at a concentration of from 25 to 55% by weight.

6. A process according to claim 1, wherein the organic solvent immiscible with water is in an amount of from 2 and 300 times the weight of the carotenoid.

7. A process according to claim 1, wherein the iodine-containing compound is selected from the group comprising iodine, iodine halide, and metal iodide.

8. A process according to claim 7, wherein said iodine-containing compound is iodine.

9. A process according to claim 7, wherein said iodinated compound is an alkali metal iodide.

10. A process according to claim 7, wherein the amount of said iodine-containing compound is from 1 to 40% by mole of the amount of the carotenoid.

11. A process according to claim 1 carried out at a pH of from 2 to 10.

12. A process according to claim 1 carried at a temperature of from minus 10° C. to 50° C.

\* \* \* \* \*